United States Patent [19]

Huth et al.

[11] Patent Number: 4,874,768
[45] Date of Patent: Oct. 17, 1989

[54] 1,2-DISUBSTITUTED ERGOLINES USEFUL FOR PRODUCING CENTRAL ANTIDOPANMINERGIC OR α2-RECEPTOR-BLOCKING ACTIVITY

[75] Inventors: Andreas Huth; Gerhard Sauer; Helmut Wachtel, all of Berlin, Fed. Rep. of Germany

[73] Assignee: Schering Aktiengesellschaft, Berlin, Fed. Rep. of Germany

[21] Appl. No.: 915,358

[22] Filed: Oct. 6, 1986

[30] Foreign Application Priority Data

Oct. 4, 1985 [DE] Fed. Rep. of Germany ....... 3535929

[51] Int. Cl.$^4$ .................... A61K 31/48; C07D 45/12
[52] U.S. Cl. ............................ 514/288; 514/269; 514/274; 544/315; 544/333; 546/67; 546/68
[58] Field of Search ................ 546/67, 68; 514/288, 514/256, 274, 269; 544/333, 315

[56] References Cited

U.S. PATENT DOCUMENTS

| | | | |
|---|---|---|---|
| 4,348,391 | 9/1982 | Stütz et al. ............... | 546/68 |
| 4,690,929 | 9/1987 | Bernardi et al. ......... | 546/68 |
| 4,731,367 | 3/1988 | Sauer et al. ............. | 514/288 |
| 4,740,509 | 4/1988 | Sauer ....................... | 514/288 |

FOREIGN PATENT DOCUMENTS

| | | | |
|---|---|---|---|
| 82808 | 6/1983 | European Pat. Off. ....... | 546/68 |
| 118848 | 9/1984 | European Pat. Off. ....... | 546/68 |
| 3413659 | 10/1985 | Fed. Rep. of Germany ....... | 546/68 |
| 3533675 | 3/1987 | Fed. Rep. of Germany ....... | 546/68 |
| 628895 | 3/1982 | Switzerland ................. | 546/68 |

*Primary Examiner*—Cecilia Shen
*Attorney, Agent, or Firm*—Millen, White & Zelano

[57] ABSTRACT

The disclosure relates to 1,2-substituted ergoline derivatives of general Formula I

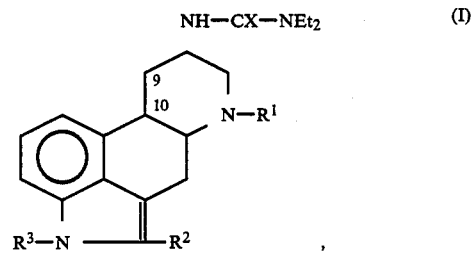

wherein
X is an oxygen or sulfur atom,
$R^1$ is a lower alkyl group,
$R^2$ is halogen, acyl, a saturated or unsaturated lower alkyl group which can optionally be substituted by $OR^4$ wherein $R^4$ is hydrogen, lower alkyl, tetrahydropyranyl or cycloalkyl, or by an optionally substituted aryl residue, an $S\text{-}R^5$-group wherein $R^5$ means a lower alkyl group which can optionally be substituted by aryl or an optionally substituted aryl residue, a

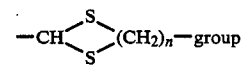

wherein n=2 o4 3, or a —CHO-group,
$R^3$ is lower alkyl or acyl, and
$C_9$-$C_{10}$ is a CC-single or a CC-double bond, and the hydrogen atom in the 10-position is in the α-location if $C_9$-$C_{10}$ is a CC-single bond, as well as the acid addition salts thereof. The compounds exhibit valuable pharmacological properties.

14 Claims, No Drawings

1,2-DISUBSTITUTED ERGOLINES USEFUL FOR PRODUCING CENTRAL ANTIDOPANMINERGIC OR α2-RECEPTOR-BLOCKING ACTIVITY

The invention relates to novel 1,2-disubstituted ergoline derivatives, their preparation, and their use as medicines.

The compounds of this invention have the general Formula I

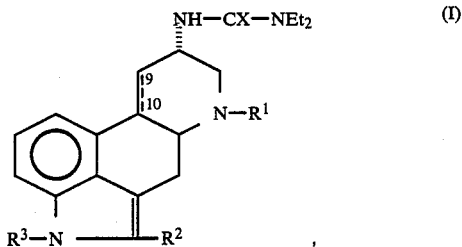

wherein
X is an oxygen or sulfur atom,
$R^1$ is a lower alkyl group,
$R^2$ is (a) halogen, (b) acyl, (c) a saturated or unsaturated lower alkyl group which can optionally be substituted by (i) $OR^4$ wherein $R^4$ is hydrogen, lower alkyl, tetrahydropyranyl or cycloalkyl, or (ii) an optionally substituted aryl residue, (d) an $S—R^5$—group wherein $R^5$ is (i) a lower alkyl group which can optionally be substituted by aryl, or (ii) an optionally substituted aryl residue,

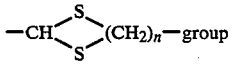

wherein n=2 or 3, or (f) a-CHO-group,
$R^3$ is lower alkyl or acyl, and
$C_9 ===== C_{10}$ is a CC-single or a CC-double bond and the hydrogen atom in the 10-position is in the α-location if $C_9 ===== C_{10}$ is a CC-single bond, as well as the acid addition salts thereof.

Lower alkyl residues are understood to mean those of up to 6 carbon atoms wherein $C_1-C_4$-alkyls are preferred, such as, for example, methyl, ethyl, isopropyl, n-propyl, n-butyl, isobutyl and tert-butyl.

If the lower alkyl residue is(unsaturated, then lower alkenyl or alkynyl residues are meant which contain preferably 2-3 carbon atoms and can be substituted by the aforementioned residues.

Acyl residues are derived from aliphatic carboxylic acids of preferably 2-4 carbon atoms, such as, for example, acetic acid, propionic acid and butyric acid.

Preferred halogens $R^2$ are chlorine, bromine or iodine.

The aromatic residue in $R^2$ contains up to 6 carbon atoms wherein one or several (e.g. up to 3) carbon atoms can be substituted by hetero atoms, such as oxygen, sulfur or nitrogen. Examples of aromatic and heteroaromatic residues are: phenyl, pyridinyl, thiophenyl, furanyl, pyrimidinyl, imidazolyl, pyrazolyl, and others.

The aromatic can be mono- or polysubstituted in any desired position, for example by lower alkyl, lower alkoxy, halogen, such as fluorine, chlorine, bromine or iodine, and other substituents.

Lower alkyl groups in the aromatic residue contain, in particular, 1-2 carbon atoms.

Preferred aralkyl residues are considered to be those of up to 2 carbon atoms in the alkyl residue, such as, for example, the benzyl or phenethyl residue. Suitable substituents are the aromatic substituents recited above.

The cycloalkyl residue preferably has 5 or 6 carbon atoms, such as, for example, cyclopentyl or cyclohexyl.

The salts of the compounds of Formula I according to this invention are acid addition salts and are derived from conventionally utilized acids. Such acids are, for example, inorganic acids, such as, for example, hydrochloric acid, nitric acid, phosphoric acid, sulfuric acid, hydrobromic acid, hydriodic acid, nitrous acid or phosphorous acid, or organic acids, e.g. aliphatic mono- or dicarboxylic acids, phenyl-substituted alkanecarboxylic acids, hydroxyalkanecarboxylic acids, or alkenedicarboxylic acids, aromatic acids, or aliphatic or aromatic sulfonic acids. Consequently, physiologically acceptable salts of these acids are, for example, the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, or naphthalene-2-sulfonate.

As compared with conventional ergolines unsubstituted in the 2-position, e.g. lisuride or terguride, the compounds of Formula I according to this invention are distinguished by a central antidopaminergic activity and/or an α2-receptor-blocking activity.

Central dopamine receptor blockage was demonstrated in an interaction test with the dopamine receptor agonist apomorphine on mice after a single i.p. pretreatment (parameter: elimination of hypothermia caused by apomorphine 5 mg/kg i.p.). Male NMRI mice were pretreated with various doses of the compound which themselves do not affect thermoregulation of the test animals, and, respectively, with a carrier medium. Thirty minutes later, all animals received apomorphine 5 mg/kg i.p. Rectal temperature was measured with the aid of a thermal probe 60 minutes after administration of compound and, respectively, of carrier medium (=30 minutes after apomorphine). While the mice pretreated with carrier medium showed hypothermia, the effect of apomorphine of lowering body temperature was overcome in dependence on the dose in animals pretreated with the compound.

Central α2-receptor blockage was demonstrated in an interaction test with the α2-receptor agonist clonidine on mice after a single i.p. pretreatment (parameter: elimination of hypothermia caused by clonidine 0.1 mg/kg i.p.). Male NMRI mice were pretreated with various doses of the compound which themselves do not affect the thermoregulation of the test animals, and with a carrier medium, respectively. Thirty minutes later, all animals received clonidine 0.1 mg/kg i.p.; rectal temperature was measured with the aid of a thermal probe 60 minutes after administration of compound and, respectively, carrier medium (=30 minutes after clonidine). While the mice pretreated with carrier medium exhibited hypothermia, the effect of clonidine of lowering body temperature was eliminated in dependence on the dose in animals pretreated with the compound.

Based on these findings, the compounds of this invention can be utilized as neuroleptics for the treatment of psychoses of the schizophrenic array of symptoms, or as antidepressants.

For using the compounds of this invention as medicinal agents, they can be brought into the form of a pharmaceutical preparation containing, in addition to the active agent, pharmaceutical, organic or inorganic, inert excipients suitable for enteral or parenteral administration, such as, for example, water, gelatin, gum arabic, lactose, amylose, magnesium stearate, talc, vegetable oils, polyalkylene glycols, etc. The pharmaceutical preparations can be present in solid form, e.g., as tablets, dragees, suppositories, capsules, or in the liquid form, for example as solutions, suspensions or emulsions. Optionally, they contain moreover auxiliary materials, such as preservatives, stabilizers, wetting agents or emulsifiers, salts for altering osmotic pressure, or buffers.

Thus, the pharmacologically active compounds of this invention can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine carbohydrates such as lactose, amylose or starch, magnesium sterate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservative, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

Generally, the compounds of this invention are dispensed in unit dosage form comprising 0.1 to 10 mg in a pharmaceutically acceptable carrier per unit dosage.

The dosage of the compounds according to this invention generally is 0.001 to 1 mg/kg/day, preferably 0.01 to 0.1, when administered to patients, e.g., humans to treat depression analogously to the known agent Idazoxan (BP 2068376).

Thus the compounds can be used as general antidepressants to treat symptoms including endogenous depression, agitated or restrained depression, idiophathic depression, lack or loss of drive, of interest, of thinking, of energy, of hope, etc., or a feeling of emptiness. They also are useful to treat excitability, subjective feelings of unrest, dysphoria or anxiety.

At these dosages they also can be administered to patients, e.g., humans, for treatment of psychosis of the schizophrenic array of symptoms, e.g., acute and chronic schizophrenia, especially with negative clinical symptoms, e.g., flattening of response, loss of drive, poverty of speech.

It will be appreciated that the actual preferred amounts of active compound in the specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

The compounds of general Formula I are produced according to methods known per se.

The process for preparing the compounds of general Formula I is characterized in that (a) a compound of general Formula II

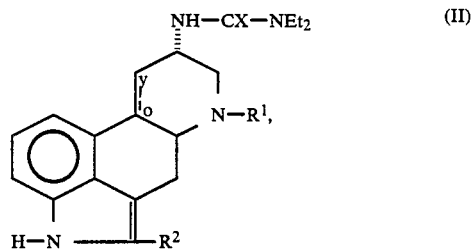

wherein

X, $R^1$, $R^2$ and $C_9$-----$C_{10}$ have the meanings given above, is acylated or, in case $R^2$ is not an S-$R^5$- or

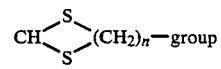

with $R^5$ and n having the meanings given above, is alkylated, (b) a compound of general Formula III

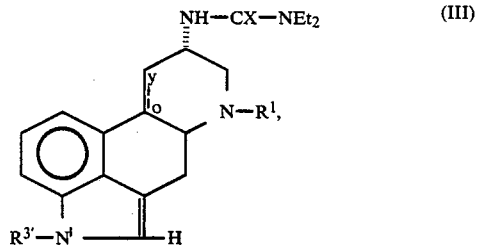

wherein

X and $R^1$ have the meanings given above and $R^{3'}$ means hydrogen or lower alkyl, is acylated, thiomethylated or halogenated and, if desired, subsequently the thus-obtained compounds of general Formula I wherein $R^2$ is halogen, (α) are converted into the corresponding 2-lithium ergoline derivative and subsequently reacted with an electrophile to compounds of general Formula I wherein $R^2$ means lower alkyl or an $SR^5$-group wherein $R^5$ has the meanings given above, or (β) are reacted in the presence of a catalyst and a base with an unsaturated lower alkyl group, optionally substituted as described above, to compounds of general Formula I wherein $R^2$ means an alkenyl or alkynyl residue, and subsequently are optionally hydrogenated entirely or partially, (c) a compound of general Formula III wherein X, R¹ and R³' have the above meanings is reacted, after a preceding formylation, with a dithiol and, if desired, subsequently the thus-obtained compounds wherein R² means;

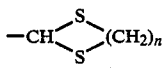

are reductively converted into the methyl group or hydrolyzed to the formyl group, and the latter is optionally reduced to —CH₂OH, and the compounds obtained according to methods (b) and (c) wherein R³'=H are acylated, and the thus-obtained compounds are optionally converted into the thioureas and/or the physiologically compatible acid addition salts are formed.

Substitution of the compounds of general Formula II in the 1-position (method a) takes place suitably in accordance with the method described by V. Illi, Synthesis 1979: 387 and Y. Kikugawa et al., Synthesis 1981: 461, by reacting, in a two-phase system, the ergoline derivative with alkyl halogenides or, respectively, carboxylic acid chlorides or anhydrides. The alkylation can also be performed in liquid ammonia according to F. Troxler et al., Helv. Chim. Acta 40: 1721 (1975).

If unsubstituted acetylene derivatives are to be alkylated in the 1-position, the proton is generally protected by one of the conventional blocking groups recited hereinbelow.

In accordance with methods (b) and (c), the desired substituents are introduced into the 2position.

For example, an acyl group R² is introduced by reacting the ergoline of general Formula III with the acyl chloride in the presence of a Lewis acid, such as, for example, AlCl₃. If the acyl chloride is not in the liquid form, then the reaction can be performed in inert solvents, e.g. chlorobenzene or nitrobenzene.

Halogenation in the 2-position can be conducted, for example, in accordance with the methods described in European Patent Application No. 0056358.

The methylthiolation can take place, for example, in an inert solvent, such as dioxane or tetrahydrofuran with a sulfonium salt, e.g. the dimethylmethylthiosulfonium fluoroborate, and is completed after 0.5–2 hours at room temperature.

However, the alkyl thiolation and aryl thiolation can also take place by way of the 2-lithium ergoline derivative and subsequent reaction with a sulfur electrophile.

For this purpose, a 2-haloergoline derivative of Formula I is reacted with a lithium organyl, preferably lithium alkyl or lithium phenyl, at low temperatures in an aprotic solvent to the corresponding 2-lithium ergoline derivative. Especially suitable as the lithium alkyl is tert-butyllithium (European Patent Application No. 160,842).

The subsequent electrophilic substitution is carried out at low temperatures, preferably between −110° C. and −50° C., in the same aprotic solvent. Suitable aprotic solvents are ethers or hydrocarbons, such as, for example, tetrahydrofuran, dioxane, diethyl ether, toluene, hexane, etc.

Preferred electrophiles that can be cited are thiosulfonic acid S-esters, e.g. methanethiosulfonic acid S-methyl ester, toluenethiosulfonic acid S-ethyl ester, toluenethiosulfonic acid S-n-propyl ester, or disulfides, e.g. dibenzyldisulfide, diphenyldisulfide, tetraisopropyl-thiuram disulfide, or lower alkyl halogenides, such as, for example, alkyl bromides and iodides or halogenated silanes, e.g. lower alkyl silanes, such as trimethylchlorosilane.

For introduction of the 2-alkenyl or 2-alkynyl group, the 2-haloergoline derivative is reacted with a monosubstituted acetylene or vinyl compound in the presence of a catalyst and a base.

The reaction takes place at temperatures from 0° C. to 120° C., preferably 70°–100° C., in an aprotic solvent, such as, for example, dimethylformamide, N-methylpyrrolidone, tetrahydrofuran, acetonitrile or dioxane.

Preferred catalysts employed are palladium compounds, such as palladium salts or palladium complex compounds. Worth mentioning are, for example, palladium(II) acetate, palladium(II) trans-dichlorobis (tri-o-tolylphosphine), or palladium(II) transdichlorobis(triphenylphosphine) and palladium (O) tetrakis(triphenylphosphine). The catalyst is used in a quantity of 0.01–0.1 mole, based on the 2-haloergoline employed.

The reaction is suitably performed under an inert gas atmosphere, such as, for example, nitrogen or argon, partially also under elevated pressure.

The addition of triaryl phosphines enhances the reaction.

Catalytic amounts of copper(I) salts, such as, for example, copper(I) iodide or copper(I) bromide, are beneficial for the ethynylation.

Suitable bases are secondary and tertiary amines, such as, for example, dimethylamine, diethylamine, piperidine, triethylamine and tri-n-butylamine.

If it is intended to produce 2-acetylene or 2-vinyl ergoline derivatives unsubstituted in the acetylene or vinyl residue, then a proton is suitably protected with a conventional blocking group, such as, for example, a trialkylsilyl group which is optionally split off during the working up of the reaction mixture.

If the blocking group is the tetrahydropyranyl residue, then an acid is utilized for the splitting-off step, e.g. pyridinium p-toluenesulfonate or dilute sulfuric acid, in an alcohol at 70°–100° C.

With the use of catalytically activated hydrogen, the 2-vinyl compounds can be hydrogenated entirely, and the 2-ethynyl compounds entirely or partially.

The complete hydrogenation is carried out in the presence of a catalyst, such as, for example, Raney nickel or palladium on various supports, such as carbon, at room temperature, optionally under elevated pressure, in an inert solvent, such as, for example, alcohols, such as methanol, ethanol, propanol, ethers, such as dioxane, diethyl ether, acids, such as glacial acetic acid, etc.

For partial hydrogenation to the double bond, the catalysts employed are, for example, palladium salts poisoned, for example, with quinoline or pyridine, but also with lead, or palladium on diverse supports (Lindlar catalysts). The solvents used are the above-mentioned alcohols or hydrocarbons.

However, a conversion of the ethynyl compound into vinyl compounds can also be accomplished by chemical addition of organometallic compounds, e.g. diisobutyl aluminum hydride, and subsequent hydrolysis. Solvents that can be used are hydrocarbons or ethers.

The thus-formed 2-ethynyl and 2-hydroxypropargyl compounds can be reacted with alkyl halogenides in the presence of lithium diisopropylamide or with phase transfer catalysts to alkyl ethynyl compounds and, respectively, alkyl propargyl ethers; in this process, the 1-position, if unsubstituted, is concomitantly alkylated.

The compound of general Formula I wherein $R^2$ means

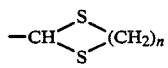

are prepared, for example, by reacting compounds of general Formula III with ethyl formate and with Lewis acids, such as Ti(IV) chloride, at room temperature in inert solvents, such as chloroform, methylene chloride, etc.

The 2-methyl compound can be obtained from the dithiolane compound by reaction with Raney nickel at room temperature, in inert solvents such as alcohols, e.g. methanol, ethanol, etc.

The 2-formyl compound can be obtained from the dithiolane compound, for example by aqueous $SiO_2$ treatment and subsequent reaction with sulfuryl chloride. The reaction is generally conducted at room temperature in inert solvents, such as chlorinated hydrocarbons, e.g. chloroform, methylene chloride, ethylene chloride, etc.

The aldehyde can be reduced to the corresponding alcohol, e.g. with $LiAlH_4$ in inert solvents, such as ethers, e.g. tetrahydrofuran, diethyl ether, etc., or with $NaBH_4$ in solvents, such as alcohols, for example methanol, ethanol, etc.

Conversion of the 8α-urea derivatives into the corresponding thiones takes place by reaction with phosphorus oxychloride and subsequent reaction with potassium xanthate. The reaction is performed at low temperatures with interim temperature elevation in inert solvents, such as ethers.

The thioreas can also be prepared by cleavage of the urea and subsequent reaction of the amine with "Thiostaab" reagent and a further amine.

All reactions are generally performed under a protective gas atmosphere, such as argon or nitrogen.

For the formation of salts, the compounds of Formula I are dissolved in a small amount of methanol or methylene chloride and combined at room temperature with a concentrated solution of the desired acid in methanol.

The starting compounds are known or can be prepared according to known methods.

The examples set forth below are to describe the process of this invention in detail.

EXAMPLE 1

3-(2-Bromo-1,1-dimethyl-8α-ergolinyl)-1,1-diethylurea

A solution is prepared from 4.18 g of 3-(2-bromo-6-methyl-8α-ergolinyl)-1,1-diethylurea (10 mmol) in 50 ml of THF; 40 mg of tetrabutylammonium hydrogen sulfate, 1 g of pulverized potassium hydroxide, and 2 ml of methyl iodide are added, and the mixture is stirred for 4 hours at room temperature. Then the organic phase is decanted, shaken with saturated bicarbonate solution for extraction, and evaporated after drying with sodium sulfate. The residue is crystallized from ethyl acetate, yielding 2.89 g (67% of theory).

$[α]_D= +10°$ (0.5% in chloroform)

The following 1-alkylations are performed analogously: from 3-(2-bromo-6-n-propyl-8α-ergolinyl)-1,1diethylurea: 3-(2-bromo-1-methyl-6-n-propyl-8α-ergolinyl)-1,1-diethylurea, crystallized as the tartrate, yield 63%

$[α]_D= +2°$ (0.5% in methanol)

1,1-diethyl-3-(1-propyl-2-iodo-6-methyl-8α-ergolinyl)urea, yield 77%; $[α]_D= +33.6°$, c=0.205; pyriiine 1,1-diethyl-3-(1-methyl-2-ethynyl-6-methyl-8α-ergolinyl)urea by way of the trimethylsilylethynyl compound and subsequent splitting off of the trimethylsilyl group with ethanolic aqueous potassium carbonate solution, mp 114°–117° C.

1,1-diethyl-3-(1-propyl-2-ethyl-6-methyl-8α-ergolinyl)urea 1,1-diethyl-3-(1-methyl-2-phenethyl-6-methyl-8α-ergolinyl)urea 1,1-diethyl-3-(1-propyl-2-phenethyl-6-methyl-8α-oergolinyl)urea 1,1-diethyl-3-(1-methyl-2-phenylethynyl-6-methyl-8α-oergolinyl)urea 1,1-diethyl-3-[1-methyl-2-(3-methoxypropynyl)-6-methyl-8α-ergolinyl]urea

EXAMPLE 2

1,1-Diethyl-3-(1,6-dimethyl-2-methylthio-8α-ergolinyl)urea

A solution is prepared from 354 mg of 1,1-diethyl-3-(1,6-dimethyl-8α-ergolinyl)urea (1 mmol) in 20 ml of THF and, at room temperature under nitrogen, 392 mg of dimethylmethylthiosulfonium tetrafluoroborate (2 mmol) and 0.24 ml of 50% strength tetrafluoroboric acid are added thereto. After 30 minutes of agitation at room temperature, the mixture is distributed between methylene chloride and bicarbonate solution, the organic phases are combined, dried with sodium sulfate, and evaporated. The crude product is chromatographed with methylene chloride on silica gel yielding, after crystallization, 276 mg (69% of theory).

$[α]_D= +11°$ (0.5% in chloroform).

In accordance with the above directions, 3-(9,10-didehydro-1,6-dimethyl-8α-ergolinyl)-1,1diethylurea gives, in the presence of tetrafluoroboric acid, 3-(9,10-didehydro-1,6-dimethyl-2-methylthio-8α-ergolinyl)-1,1-diethylurea in a 55% yield.

EXAMPLE 3

3-(2-Bromo-9,10-didehydro-1,6-dimethyl-8α-ergolinyl)-1,1-diethylurea

A solution is prepared from 352 mg of 3(9,10-didehydro-1,6-dimethyl-8α-ergolinyl)-1,1diethylurea (1 mmol) in 20 ml of anhydrous dioxane; the mixture is combined with 484 mg of pyrrolidone hydroperbromide (1.5 mmol) and agitated for 30 minutes at room temperature. The reaction mixture is then poured into a saturated bicarbonate solution, extracted with methylene chloride, and the organic phase is dried with sodium sulfate. After evaporation of the solvent, the residue is chromatographed on silica gel, thus isolating, after crystallization, 345 mg of the desired compound (80% of theory). $[α]_D= +299°$ (0.5% in chloroform).

EXAMPLE 4

1,1-Diethyl-3-(1,6-dimethyl-2-phenylthio-8α-ergolinyl)urea

Under argon, 0.3 ml (1.5 mmol) of distilled hexamethyldisilazane is added to 4 ml of anhydrous, freshly distilled toluene, and the mixture is cooled to 0° C. Then 0.85 ml (1.4 mmol) of 15% strength butyllithium in hexane is added dropwise and the mixture further stirred for 15 minutes at 0° C. A solution of 432 mg of 3-(2-bromo-1,6-dimethyl-8α-ergolinyl)-1,1-diethylurea (1 mmol) in 50 ml of anhydrous, freshly distilled toluene is added to this mixture, and the latter is stirred for another 15 minutes at 0° C. After addition of 1 ml of freshly distilled tetramethylethylenediamine, the batch is cooled to −90° C. At this temperature, 5 ml (7 mmol) of tert-butyllithium (14% in hexane) is added and the mixture is stirred for another 2 minutes before adding 1 g of diphenyldisulfide (5 mmol). After 2 hours of agitation at −70° C., water is added to work up the reaction mixture. Extraction is performed with ethyl acetate. The organic phases are washed with saturated sodium bicarbonate solution and water. The combined ethyl acetate phases are dried over sodium sulfate and concentrated. After crystallization from ethyl acetate and tert-butylmethyl ether, 180 mg of the desired compound is obtained (39% of theory).

In an entirely analogous way, the following ureas are prepared from the same starting material: with dibenzyldisulfide: 3-(2-benzylthio-1,6 dimethyl-8α-ergolinyl)-1,1-diethylurea, yield 47%, with p-toluenethiosulfonic acid S-n-propyl ester: 1,1-diethyl-3-(1,6-dimethyl-2-n-propylthio-8α-oergolinyl)urea, yield 65%.

Using 3-(2-bromo-9,10-didehydro-1,6-dimethyl-8α-ergolinyl)-1,1-diethylurea and reacting same with diphenyldisulfide, 3-(9,10-didehydro-1,6-dimethyl-2-phenylthio-8α-ergolinyl)-1,1-diethylurea is obtained in a 47% yield.

EXAMPLE 5

At room temperature under argon, 7 ml of formic acid ethyl ester and 3.6 ml (44 mmol) of ethanedithiol are added in succession to a solution of 6.9 g of 1,1-diethyl-3-(1,6-dimethyl-8α-ergolinyl)urea in 200 ml of chloroform. Then, 8.8 ml (80 mmol) of titanium(IV) chloride dissolved in 100 ml of chloroform is added gradually dropwise to the reaction mixture and the latter is stirred for 20 hours at room temperature. Although the starting material at this point in time has not as yet been completely reacted, the reaction mixture is worked up to avoid further formation of the disubstituted compound. For this purpose, the reaction mixture is cooled in an ice bath and combined, in succession, dropwise with 50 ml of methanol and 40 ml of water. Then the mixture is made alkaline with 25% strength ammonia solution and extracted with methylene chloride. The organic phases are washed with water and dried over magnesium sulfate. The evaporated residue is crystallized under boiling heat from methanol/ethyl acetate, thus obtaining 3.0 g of 1,1-diethyl-3[2-(1,3-dithiolan-2-yl)-1,6-dimethyl-8α-ergolinyl]urea (37% yield).

EXAMPLE 6

7.5 ml of a Raney nickel suspension is washed four times with respectively 30 ml of methanol. Thereafter, 15 ml of methanol and then a solution of 690 mg (1.5 mmol) of 1,1-diethyl-3-[2-(1,3-dithiolan-2-yl)-1,6-dimethyl-8α-ergolinyl]urea in 15 ml of methanol are added thereto. The mixture is agitated for 3 hours at room temperature and then once more 7.5 ml of a Raney nickel suspension, previously washed as above four times with respectively 30 ml of methanol, is added thereto. After another 2 hours of agitation at room temperature, the catalyst is filtered off via a silica gel column and washed thoroughly with methanol. The filtrate is evaporated and the residue crystallized from methanol/ethyl acetate, thus obtaining 150 mg of 1,1-diethyl-3-(1,2,6-trimethyl8α-ergolinyl)urea (27% yield).

EXAMPLE 7

Under argon, 2.12 g (5 mmol) of 1,1-diethyl-3-[2-(1,3-dithiolan-2-yl)-6-methyl-8ergolinyl]urea is dissolved in 40 ml of chloroform. Then 3.5 g of silica gel is added and, under vigorous agitation, 3.5 ml of water is introduced dropwise. During a time period of 30 minutes, a solution of 1.18 ml of sulfuryl chloride in 30 ml of chloroform is added dropwise. After 3 hours of agitation at room temperature, 7.5 g of potassium carbonate is added and the mixture vigorously stirred for 20 minutes. The precipitate is filtered off and rinsed with chloroform. The precipitate is moistened with ethanol and introduced into 300 ml of saturated sodium chloride solution which is then repeatedly extracted with chloroform. The chloroform extracts and the chloroform filtrate are dried together over magnesium sulfate and evaporated. Subsequent crystallization takes place from ethyl acetate, thus isolating 1.16 g of 1,1-diethyl-3-(6-methyl-2-formyl-8α-ergolinyl)urea (61% yield).

EXAMPLE 8

Under argon, 320 mg (8 mmol) of lithium aluminum hydride is suspended in 20 ml of absolute, freshly distilled tetrahydrofuran. At room temperature, a solution of 1.53 g (4 mmol) of 1,1-diethyl-3(1,6-dimethyl-2-formyl-8α-ergolinyl)urea in 40 ml of freshly distilled, absolute tetrahydrofuran is added dropwise. Subsequently the mixture is stirred for 1 ¼ hours at room temperature. The batch is then cooled in an ice bath and combined with 20 ml of 1N hydrochloric acid. To this is added 20 ml of 2N tartaric acid and the batch is layered over with ethyl acetate. For neutralizing, 80 ml of 2N ammonia solution is added dropwise. The ethyl acetate phase is separated and the aqueous phase additionally extracted with ethyl acetate. The combined ethyl acetate phases are dried over sodium sulfate. The concentrated crude product is chromatographed under pressure on silica gel with methylene chloride/methanol 95:5. The crude product (1.0 g) is crystallized from ethyl acetate, thus obtaining 0.72 g of 1,1-diethyl-3-(1,6-dimethyl-2-hydroxymethyl-8α-ergolinyl)urea (47% yield).

EXAMPLE 9

1,1-Diethyl-3-(2-iodo-1-acetyl-6-methyl-8α-ergolinyl)urea 1.05 g of 1,1-diethyl-3-(2-iodo-6-methyl-8α-ergolinyl)urea is stirred for 3 hours at room temperature in 90 ml of methylene chloride with 115 mg of tetrabutylammonium hydrogen sulfate, 0.18 ml of acetyl chloride and 139 mg of pulverized potassium hydroxide pellets. After suctioning off over kieselguhr, the mixture is once again combined with the same amounts of acetyl chloride, pulverized potassium hydroxide and tetrabutylammonium hydrogen sulfate and stirred for one hour at room temperature. After combining with ice water, the mixture is neutralized with sodium bicarbonate and extracted by shaking. The organic phase is dried, filtered, and concentrated. The residue is chromatographed over silica gel with methylene chloride:ethanol=10:1 as the eluent, thus obtaining 500 mg of 1,1-diethyl-3-(2-iodo-1-acetyl-6-methyl-8α-ergolinyl)urea as an oil. $[\alpha]_D = +40°$ (c=0.2 pyridine).

1,1-Diethyl-3-[1-acetyl-2-[(3-tetrahydropyran-2-yloxy)-1-propynyl]-6-methyl-8α-ergolinyl]urea is produced analogously.

EXAMPLE 10

1,1-Diethyl-3-(2-vinyl-1-propyl-6-methyl-8α-ergolinyl)urea

In a small autoclave, 1.15 g of 1,1-diethyl-3-(2-iodo-1-propyl-6-methyl-8α-ergolinyl)urea is heated under argon for 3 hours to a bath temperature of 115° C. in 10 ml of dimethylformamide with 10 ml of triethylamine, 53.5 mg of triorthotolylphosphine, 39.4 mg of palladium(II) chloride and 1.34 ml of vinyltrimethylsilane. After evaporation, the mixture is distributed in methylene chloride/sodium bicarbonate solution. The organic phase is evaporated and chromatographed over silica gel with ethyl acetate: ethanol=3:1 as the eluent, thus obtaining 218 mg of 1,1-diethyl-3-(2-trimethylsilylvinyl-1-propyl-6-methyl-8α-ergolinyl)urea and 230 mg of 1,1-diethy-3-(2-vinyl-1-propyl-6-methyl-8α-ergolinyl)urea as oils.

EXAMPLE 11

1,1-Diethyl-3-(2-ethyl-1-propyl-6-methyl-8α-ergolinyl)urea

At room temperature and under hydrogen normal pressure, 150 mg of 1,1-diethyl-3-(2-vinyl-1-propyl-6-methyl-8α-ergolinyl)urea is hydrogenated in 20 ml of ethanol with 0.1 g of Raney nickel (B 115 Z). After the catalyst has been filtered off over kieselguhr, evaporation of the filtrate, and chromatography over silica gel with toluene:ethanol:water=80:20:1 as the eluent, 65 mg of 1,1-diethyl-3-(2-ethyl-1-propyl-6-methyl-8α-ergolinyl)urea is obtained as an oil.

EXAMPLE 12

3-(6-Methyl-1-propyl-2-ethyl-8α-ergolinyl)-1,1-diethyl-thiourea 200 mg of 1,1-diethyl-3-(2-ethyl-6-methyl-1-propyl-8α-ergolinyl)urea is combined in 10 ml of methylene chloride with 0.13 ml of phosphorus oxychloride at −12° C. Within one hour, the batch is allowed to warm up to room temperature and is stirred for 16 hours at this temperature. After evaporation, the mixture is extracted by stirring with ether, suctioned off, and dried under vacuum over KOH pellets. The dried material is then combined with a solution of 245 mg of potassium xanthate in 15 ml of acetonitrile at −10° C. and further stirred for 2 hours at room temperature. After evaporation, the mixture is distributed in methylene chloride/sodium bicarbonate solution, the organic phase is concentrated, and the residue is chromatographed over silica gel with methylene chloride:ethanol=10:1 as the eluent. Recrystallization from a small amount of ethanol/hexane yields 100 mg of 3-(6-methyl-1-propyl-2-ethyl-8α-ergolinyl)-1,1-diethylthiourea, mp 173°–175° C. $[\alpha]_D = +48°$ (c=0.2 pyridine).

EXAMPLE 13

1,1-Diethyl-3-(2-trimethylsilylethynyl-1-acetyl-6-methyl-8α-ergolinyl)urea

Under argon, 260 mg of 1,1-diethyl-3-(2-iodo-1-acetyl-6-methyl-8α-ergolinyl)urea is heated to 60° C. for 1.5 hours in 3 ml of dimethylformamide with 6 ml of triethylamine, 0.5 ml of trimethylsilylacetylene, 6 mg of copper(I) iodide, and 15 mg of bis(triorthotolylphosphine)palladium(II) dichloride. After evaporation, the mixture is distributed in ethyl acetate/bicarbonate solution. The organic phase is chromatographed, after evaporation, over silica gel with methylene chloride:methanol=9:1, thus obtaining 100 mg of 1,1-diethyl-3-(2-trimethylsilylethynyl-1-acetyl-6-methyl-8α-ergolinyl)urea as an oil.

EXAMPLE 14

1,1-Diethyl-3-(2-ethynyl-1-propyl-6-methyl-8α-ergolinyl)urea

Under argon, 109 mg of 1,1-diethyl-3-(2-ethynyl-6-methyl-8α-ergolinyl)urea in 5 ml of absolute tetrahydrofuran is added dropwise at −30° C. to a solution of lithium diisopropylamide, prepared from 0.15 ml of diisopropylamine and 1.8 ml of 0.6-molar n-butyllithium solution (hexane) in 3 ml of absolute tetrahydrofuran at 0° C. within 15 minutes. After 30 minutes of agitation at −30° C., 0.07 ml of propyl iodide is added thereto. The mixture is stirred for one hour at −20° C. and overnight at room temperature. After evaporation, the mixture, after adding sodium bicarbonate solution and a small amount of ethanol, is extracted by shaking with ethyl acetate. The organic phase is concentrated and chromatographed over silica gel with toluene:glacial acetic acid:water=10:10:1, thus obtaining 30 mg of 1,1-diethyl-3-(2-ethynyl-1-propyl-6-methyl-8α-ergolinyl)urea as an oil.

Pursuant to the same method, using the same starting material as above, 1,1-diethyl-3-(2-propynyl-1,6-dimethyl-8α-ergolinyl)urea is obtained as an oil.

We claim:

1. A 1, 2-substituted ergoline compound of general formula I

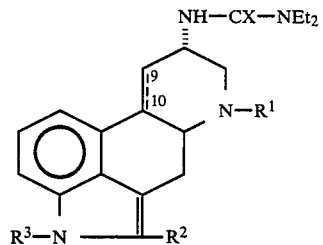

wherein

X is an oxygen or sulfur atom,

R¹ is a lower alkyl group,

R² is (a) halogen; (b) a C₂₋₄-carboxylic acid; (c) a lower alkyl, lower alkenyl or alkynyl group; (d) an alkyl, alkynyl or alkenyl group which is substituted by (i) OR₄ wherein R⁴ is hydrogen, lower alkyl, tetrahydropyranyl or C₅₋₆-cycloalkyl, (ii) phenyl, pyridinyl, thiophenyl, furanyl, pyrimidinyl, imidazolyl or pyrazolyl, (iii) phenyl, pyridinyl, thiophenyl, furanyl, pyrimidinyl, imidazolyl or pyrazolyl substituted by a lower alkyl, lower alkoxy or halogen group; (e) an S-R⁵ group wherein R⁵ means (i) a lower alkyl group, (ii) a lower alkyl group substituted by phenyl, pyridinyl, thiophenyl, furanyl, pyrimidinyl, imidazolyl, or pyrazolyl in turn substituted by a lower alkyl, lower alkoxy or halogen group;

(f) a

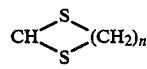

group wherein n=2 or 3; or
(g) a —CHO group,
$R_3$ is lower alkyl or the acyl group of a $C_{2-4}$-carboxylic acid, and
$C_9 ==== C_{10}$ is a CC-single or a CC-double bond, and the hydrogen atom in the 10-position is in the α -location if $C_9 ==== C_{10}$ is a CC-single bond, as well as a physiologically compatible acid addition salt thereof.

2. 3-(2-Bromo-1,6-dimethyl-8α-ergolinyl) 1,1-diethylurea, 3-(2-bromo-1-methyl-6-n-propyl-8α-ergolinyl)1,1-diethylurea, 1,1-diethyl-3-(1-propyl-2-iodo-6-methyl-8α-ergolinyl)urea, 1,1-diethyl-3-(1-methyl-2-ethynyl-6-methyl-8α-ergolinyl)urea, 1,1-diethyl-3-(1-propyl-2-ethyl-6-methyl-8oergolinyl)urea, 1,1-diethyl-3-(1-methyl-2-phenethyl-6-methyl-8α-ergolinyl)urea, 1,1-diethyl-3-(1-methyl-2-phenylethynyl-6-methyl-8α-ergolinyl)urea, 1,1-diethyl-3-[1-methyl-2-(3-methoxypropynyl)-6-methyl-8α-ergolinyl]urea, 1,1-diethyl-3-(1,6-dimethyl-2-methylthio-8α-ergolinyl)urea, 3-(9,10-didehydro-1,6-dimethyl-2-methylthio-8α-ergolinyl)-1,1-diethylurea, 3-(2-bromo-9,10-didehydro,-1,6-dimethyl-8α-ergolinyl)1,1-diethylurea, 1,1-diethyl-3-(1,6-dimethyl-2-phenylthio-8α-ergolinyl)urea, 3-(2-benzylthio-1,6-dimethyl-8α-ergolinyl)-1,1diethylurea, 1,1-diethyl-3-(1,6-dimethyl-2-n-propylthio-8oergolinyl-)urea, 3-(9,10-didehydro-1,6-dimethyl-2-phenylthio-8α-ergolinyl)-1,1-diethylurea, 1,1-diethyl-3-[2-(1,3-dithiolan-2-yl)-1,6-dimethyl-8α-ergolinyl]urea, 1,1-diethyl-3-(1,2,6-trimethyl-8α-ergolinyl)urea, 1,1-diethyl-3-(6-methyl-2-formyl-8α-ergolinyl)urea, 1,1-diethyl-3-(1,6-dimethyl-2-hydroxymethyl-8α-ergolinyl)urea, 1,1-diethyl-3-(2-iodo-1-acetyl-6-methyl-8α-ergolinyl)urea, 1,1-diethyl-3-[1-acetyl-2-[(3-tetrahydropyran-2-yloxy)1-propynyl]-6-methyl-8α-ergolinyl]urea, 1,1-diethyl-3-(2-vinyl-1-propyl-6-methyl-8α-ergolinyl)urea, 1,1-diethyl-3-(2-ethyl-1-propyl-6-methyl-8α-ergolinyl)urea, 3-(6-methyl-1-propyl-2-ethyl-8α-ergolinyl)-1,1diethylthiourea, 1,1-diethyl-3-(2-ethynyl-1-propyl-6-methyl-8⊕-ergolinyl)urea, 1,1-diethyl-3-(2-propynyl-1,6-dimethyl-8α-ergolinyl)urea.

3. A compound according to claim 1, wherein $R_2$ is $C_{1-4}$-alkyl or $C_{2-3}$-alkenyl.

4. A compound according to claim 1, wherein $R^2$ or $R^3$ is acetic acid, propionic acid or butyric acid.

5. A compound according to claim 1, wherein $R^2$ is chlorine, bromine or iodine.

6. A compound according to claim 1, wherein $R^2$ is phenyl, pyridinyl, thiophenyl, furanyl, pyrimidinyl, imidazolyl, pyrazolyl, benzyl or phenethyl.

7. A compound according to claim 1, wherein $R^1$ is alkyl and $R^2$ is halogen.

8. A compound according to claim 7, wherein $R^1$ is methyl and $R^2$ is bromo.

9. A pharmaceutical composition useful for producing central antidopaminergic or $α_2$-receptor-blocking activity, comprising an effective amount of a compound of claim 1 and a pharmaceutically acceptable carrier.

10. A method of producing central antidopaminergic or $α_2$-receptor-blocking activity, comprising administering an effective amount of a compound of claim 1.

11. A method of producing central antidopaminergic and $α_2$-receptor-blocking activity, comprising administering an effective amount of a compound of claim 1.

12. A method of producing an antidepressant effect, comprising administering an effective amount of a compound of claim 1.

13. A method of producing a neuroleptic effect, comprising administering an effective amount of a compound of claim 1.

14. A method of treating schizophrenia, comprising administering an effective amount of a compound of claim 1.

* * * * *

UNITED STATES PATENT AND TRADEMARK OFFICE
CERTIFICATE OF CORRECTION

PATENT NO. : 4,874,768

DATED : October 17, 1989

INVENTOR(S) : ANDREAS HUTH ET AL

It is certified that error appears in the above-identified patent and that said Letters Patent is hereby corrected as shown below:

Column 13, claim 2, line 20:

reads "(1-propyl-2-ethyl-6-methyl-8oergolinyl)urea, 1,1-dieth-"

should read -- (1-propyl-2-ethyl-6-methyl-8αergolinyl)urea, 1,1-dieth- --

Column 13, claim 2, line 31:

reads "diethyl-3-(1,6-dimethyl-2-n-propylthio-8oergolinyl-"

should read -- diethyl-3-(1,6-dimethyl-2-n-propylthio-8αergolinyl- --

Column 14, claim 2, line 5:

reads "8⊕-ergolinyl)urea,   1,1-diethyl-3-(2-propynyl-1,6-"

should read -- 8α-ergolinyl)urea,   1,1-diethyl-3-(2-propynyl-1,6- --

Signed and Sealed this

Twenty-fifth Day of September, 1990

Attest:

HARRY F. MANBECK, JR.

Attesting Officer

Commissioner of Patents and Trademarks